United States Patent
Awasthi et al.

(10) Patent No.: US 12,405,488 B2
(45) Date of Patent: Sep. 2, 2025

(54) OPHTHALMIC DEVICES

(71) Applicant: Bausch + Lomb Ireland Limited, Dublin (IE)

(72) Inventors: Alok Kumar Awasthi, Pittsford, NY (US); Kristen Rae Hovinga, Honeoye Falls, NY (US); Emily Abrams Gabriel, Pittsford, NY (US); Kevin Jacob DeRyke, Webster, NY (US); Jade J. Russell, Perry, NY (US); Alana Ingham, Hilton, NY (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 639 days.

(21) Appl. No.: 17/836,258

(22) Filed: Jun. 9, 2022

(65) Prior Publication Data
US 2023/0097637 A1   Mar. 30, 2023

Related U.S. Application Data

(60) Provisional application No. 63/239,246, filed on Aug. 31, 2021.

(51) Int. Cl.
*G02C 7/10* (2006.01)
*A61L 12/14* (2006.01)
(Continued)

(52) U.S. Cl.
CPC ............ *G02C 7/107* (2013.01); *A61L 12/147* (2013.01); *C07C 301/02* (2013.01);
(Continued)

(58) Field of Classification Search
CPC .... G02C 7/107; G02C 7/049; G02C 2202/24; G02C 7/104; A61L 12/147; C07C 301/02;
(Continued)

(56) References Cited

U.S. PATENT DOCUMENTS 3,408,429 A   10/1968   Wichterle
3,660,545 A   5/1972   Wichterle
(Continued)

FOREIGN PATENT DOCUMENTS

CN   113248466 A   8/2021
KR   1020100069393 A   6/2010
(Continued)

OTHER PUBLICATIONS

Lai, Yu-Chin, "The Role of Bulky Polysiloxanylalkyl Methacryates in Polyurethane-Polysiloxane Hydrogels," Journal of Applied Polymer Science, 1996, pp. 1193-1199, vol. 60.

*Primary Examiner* — Tuyen Tra
(74) *Attorney, Agent, or Firm* — Michael E. Carmen; John E. Thomas

(57) ABSTRACT

A method for preparing an ophthalmic device for slowing, inhibiting or preventing myopia progression involves (a) soaking an ophthalmic device in one or more first solvent solutions to swell the ophthalmic device; (b) soaking the swelled ophthalmic device in one or more second solvents solutions comprising one or more red-light blocking compounds blocking greater than about 5% to about 25% of red-light transmission through the ophthalmic device at a wavelength of from about 550 nanometers (nm) to about 800 nm to de-swell the swelled ophthalmic device and entrap the one or more red-light blocking compounds in the de-swelled ophthalmic device; and (c) sterilizing the de-swelled ophthalmic device.

20 Claims, 1 Drawing Sheet

Example 1

(51) Int. Cl.
    *C07C 301/02*    (2006.01)
    *C07D 205/06*    (2006.01)
    *C07D 279/08*    (2006.01)
    *C07D 403/10*    (2006.01)
    *C07D 403/14*    (2006.01)
    *C07D 409/06*    (2006.01)
    *G02C 7/04*    (2006.01)

(52) U.S. Cl.
    CPC ......... *C07D 205/06* (2013.01); *C07D 279/08* (2013.01); *C07D 403/10* (2013.01); *C07D 403/14* (2013.01); *C07D 409/06* (2013.01); *G02C 7/049* (2013.01); *G02C 2202/24* (2013.01)

(58) Field of Classification Search
    CPC .. C07D 205/06; C07D 279/08; C07D 403/10; C07D 403/14; C07D 409/06; G02B 5/223
    See application file for complete search history.

(56) References Cited

U.S. PATENT DOCUMENTS

| | | |
|---|---|---|
| 4,113,224 A | 9/1978 | Clark et al. |
| 4,136,250 A | 1/1979 | Mueller et al. |
| 4,153,641 A | 5/1979 | Deichert et al. |
| 4,197,266 A | 4/1980 | Clark et al. |
| 4,468,229 A | 8/1984 | Su |
| 4,555,732 A | 11/1985 | Tuhro |
| 4,740,533 A | 4/1988 | Su et al. |
| 4,910,277 A | 3/1990 | Bambury et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Nandu et al. |
| 5,271,876 A | 12/1993 | Ibar |
| 5,310,779 A | 5/1994 | Lai |
| 5,321,108 A | 6/1994 | Kunzler et al. |
| 5,358,995 A | 10/1994 | Lai et al. |
| 5,387,662 A | 2/1995 | Kunzler et al. |
| 5,449,729 A | 9/1995 | Lai |
| 5,512,205 A | 4/1996 | Lai |
| 5,610,252 A | 3/1997 | Bambury et al. |
| 5,616,757 A | 4/1997 | Bambury et al. |
| 5,708,094 A | 1/1998 | Lai et al. |
| 5,710,302 A | 1/1998 | Kunzler et al. |
| 5,714,557 A | 2/1998 | Kunzler et al. |
| 5,908,906 A | 6/1999 | Kunzler et al. |
| 5,944,853 A | 8/1999 | Molock et al. |
| 7,915,323 B2 | 3/2011 | Awasthi et al. |
| 7,994,356 B2 | 8/2011 | Awasthi et al. |
| 8,420,711 B2 | 4/2013 | Awasthi et al. |
| 8,703,891 B2 | 4/2014 | Broad |
| 8,827,447 B2 | 9/2014 | Awasthi et al. |
| 8,865,929 B2 | 10/2014 | Xu et al. |
| 8,937,110 B2 | 1/2015 | Alli et al. |
| 8,937,111 B2 | 1/2015 | Alli et al. |
| 9,039,174 B2 | 5/2015 | Awasthi et al. |
| 9,156,934 B2 | 10/2015 | Alli et al. |
| 9,244,197 B2 | 1/2016 | Alli et al. |

FOREIGN PATENT DOCUMENTS

| | | |
|---|---|---|
| KR | 1020110054264 A | 5/2011 |
| WO | 9631792 A1 | 10/1996 |
| WO | 2019155244 A1 | 8/2019 |
| WO | 2019212657 A1 | 11/2019 |

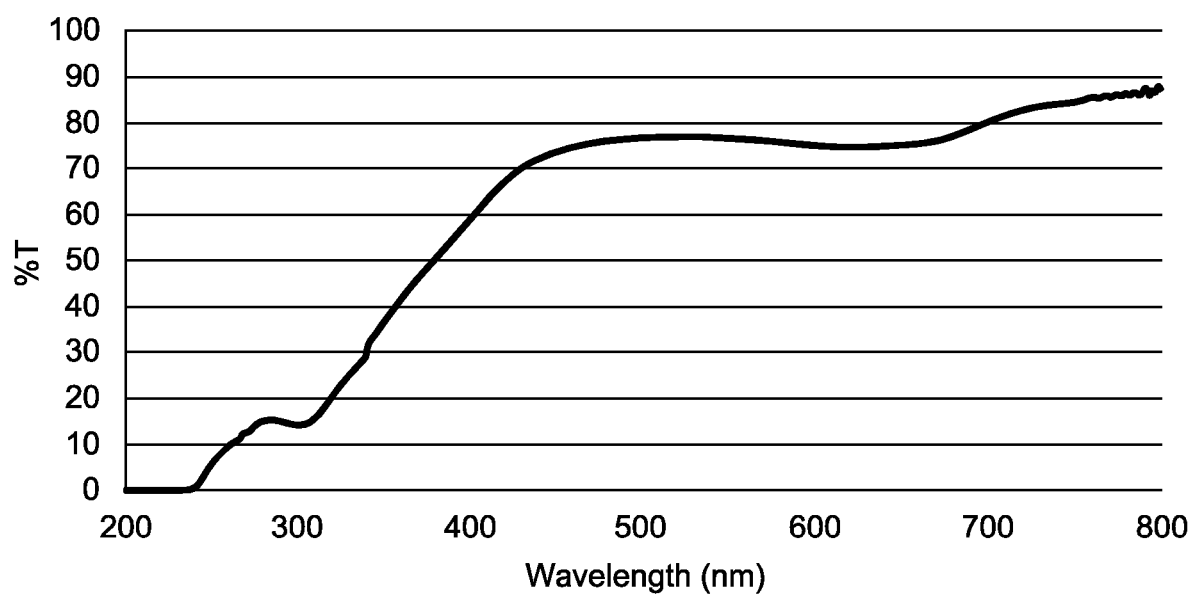

OPHTHALMIC DEVICES

PRIORITY CLAIM

The present application claims priority to U.S. Provisional Patent Application Ser. No. 63/239,246, entitled "Ophthalmic Devices," filed Aug. 31, 2021, the content of which is incorporated by reference herein in its entirety.

BACKGROUND

This disclosure generally relates to ophthalmic devices such as contact lenses for slowing, inhibiting or preventing myopia progression.

Ophthalmic devices such as contact lenses are made of various polymeric materials, including rigid gas permeable materials, soft elastomeric materials, and soft hydrogel materials. The majority of contact lenses sold today are made of soft hydrogel materials. Hydrogels are a cross-linked polymeric system that absorb and retain water, typically 10 to 80 percent by weight. Hydrogel lenses are commonly prepared by polymerizing a lens-forming monomeric mixture. In the case of silicone hydrogel lenses, a silicone-containing monomer is copolymerized with a hydrophilic monomer.

In the field of ophthalmic devices, various physical and chemical properties such as, for example, oxygen permeability, wettability, material strength and stability are but a few of the factors that must be carefully balanced in order to provide a useable contact lens. For example, since the cornea receives its oxygen supply from contact with the atmosphere, oxygen permeability is an important characteristic for certain contact lens material. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

SUMMARY

In accordance with an exemplary embodiment, a method for making an ophthalmic device for slowing, inhibiting or preventing myopia progression comprises:
(a) soaking an ophthalmic device in one or more first solvent solutions to swell the ophthalmic device;
(b) soaking the swelled ophthalmic device in one or more second solvent solutions comprising one or more red-light blocking compounds blocking greater than about 5% to about 25% of red-light transmission through the ophthalmic device at a wavelength of from about 550 nanometers (nm) to about 800 nm to de-swell the swelled ophthalmic device and entrap the one or more red-light blocking compounds in the de-swelled ophthalmic device; and
(c) sterilizing the de-swelled ophthalmic device.

In accordance with another illustrative embodiment, an ophthalmic device for slowing, inhibiting or preventing myopia progression comprises one or more red-light blocking compounds blocking greater than about 5% to about 25% of red-light transmission through the ophthalmic device at a wavelength of from about 550 nm to about 800 nm entrapped in a polymerization product of a monomeric mixture comprising one or more ophthalmic device-forming monomers.

In accordance with yet another illustrative embodiment, a method for slowing, inhibiting or preventing myopia progression in a subject in need thereof comprises (a) providing an ophthalmic device comprising one or more red-light blocking compounds blocking greater than about 5% to about 25% of red-light transmission through the ophthalmic device at a wavelength of from about 550 nm to about 800 nm entrapped in a polymerization product of a monomeric mixture comprising one or more ophthalmic device-forming monomers; and (b) inserting the ophthalmic device into an eye of the subject.

BRIEF DESCRIPTION OF THE DRAWING

Exemplary embodiments of the present disclosure will be described below in more detail, with reference to the accompanying drawing, of which:

FIG. 1 is a graph illustrating the percent transmission of red-light through the lens of Example 1.

DETAILED DESCRIPTION

Various illustrative embodiments described herein are directed to ophthalmic devices having one or more red-light blocking compounds entrapped therein for slowing, inhibiting or preventing myopia progression in a subject in need thereof, e.g., a human. In general, natural light consists of different monochromatic lights with different wavelengths, which may not focus on the same plane on the retina. A longer wavelength monochromatic light can focus on the plane behind the retina whereas a shorter wavelength monochromatic light can focus on the plane in front of the retina. The different focuses of the lights may contribute to a backward displacement of the retina toward the eye's image plane leading to elongation of the eye. This can result in various pathologies including myopia.

Myopia ("nearsightedness") is a vision condition where objects near to a viewer appear clear, but objects that are spaced farther away from the viewer get progressively blurred. Myopia can be caused by multiple reasons. One factor in many cases of myopia is an elongated axial length of the eye. Myopia occurs when the focal point of the focused light is formed before the retina. In other words, the focal point of the light rays entering the eye stop short of the retina. Thus, myopic eyes focus in front of the retinal plane. Myopia typically develops because the axial length of the eye grows to be longer than the focal length of the optical components of the eye, that is, the eye grows too long.

It is believed that excessive stimulation of L cones in a person's eye (especially in children), may result in non-optimal eye lengthening and myopia. By spectrally filtering red-light using an ophthalmic device containing one or more red-light blocking compounds, myopia can be further reduced in a wearer. However, present dyes (or colorants) of such red-light blocking compounds typically used to manufacture tinted soft contact lenses often leach out and the lenses lose their original tint when subjected to sterilization conditions or during prolonged storage. Thus, there is a need for an improved ophthalmic device which can filter and/or block red-light thereby slowing, inhibiting or preventing myopia in a wearer of the ophthalmic device.

Accordingly, the ophthalmic devices described herein overcome the foregoing problems and advantageously provide for at least one of slowing, inhibiting or preventing myopia progression by blocking greater than about 5% and up to about 25% of red-light transmission through the ophthalmic device at a wavelength of from about 550 nanometers (nm) to about 800 nm. In non-limiting illustrative embodiments, an ophthalmic device for slowing, inhibiting or preventing myopia progression in subject need thereof comprises one or more red-light blocking compounds blocking greater than about 5% to about 25% of red-light transmission through the ophthalmic device at a wavelength of from about 550 nm to about 800 nm entrapped in a polymerization product of a monomeric mixture comprising one or more ophthalmic device-forming monomers The ophthalmic devices disclosed herein are intended for direct contact with body tissue or body fluid. As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens, soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

As used herein, the term "(meth)" denotes an optional methyl substituent. Thus, for example, terms such as "(meth) acrylate" denotes either methacrylate or acrylate, and "(meth)acrylamide" denotes either methacrylamide or acrylamide.

The ophthalmic devices can be formed of any material known in the art capable of forming an ophthalmic device. In one embodiment, an ophthalmic device includes a device formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl(meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1,3-dioxol. Representative examples of suitable bulk materials include, but are not limited to, lotrafilcon A, neofocon, pasifocon, telefocon, silafocon, fluorsilfocon, paflufocon, silafocon, elastofilcon, fluorofocon or Teflon® AF materials, such as Teflon® AF 1600 or Teflon® AF 2400 which are copolymers of about 63 to about 73 mol % of perfluoro-2, 2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, an ophthalmic device includes a device which is formed from material hydrophilic per se, since reactive groups, e.g., carboxy, carbamoyl, sulfate, sulfonate, phosphate, amine, ammonium or hydroxy groups, are inherently present in the material and therefore also at the surface of an ophthalmic device manufactured therefrom. Such devices are formed from materials known in the art and include, by way of example, unsaturated carboxylic acids, acrylamides, vinyl lactams, poly(alkyleneoxy)(meth) acrylates, hydroxyl-containing-(meth)acrylates, hydrophilic vinyl carbonates, hydrophilic vinyl carbamates, hydrophilic oxazolones, and poly(alkene glycols) functionalized with polymerizable groups and the like and mixtures thereof. Representative examples of unsaturated carboxylic acids include methacrylic acid, acrylic acid and the like and mixtures thereof. Representative examples of amides include alkylamides such as N,N-dimethylacrylamide, N,N-dimethylmethacrylamide and the like and mixtures thereof. Representative examples of cyclic lactams include N-vinyl-2-pyrrolidone, N-vinyl caprolactam, N-vinyl-2-piperidone and the like and mixtures thereof. Representative examples of hydroxyl-containing (meth)acrylates include 2-hydroxyethyl methacrylate, glycerol methacrylate and the like and mixtures thereof. Representative examples of functionalized poly(alkene glycols) include poly(diethylene glycols) of varying chain length containing monomethacrylate or dimethacrylate end caps. In one embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. Mixtures of the foregoing non-silicone-containing hydrophilic monomers can also be used in the monomeric mixtures herein.

Representative examples of suitable hydrophilic bulk materials include, but are not limited to, polymacon, tefilcon, methafilcon, deltafilcon, bufilcon, phemfilcon, ocufilcon, focofilcon, etafilcon, hefilcon, vifilcon, tetrafilcon, perfilcon, droxifilcon, dimefilcon, isofilcon, mafilcon, nelfilcon, atlafilcon and the like. Examples of other suitable bulk materials include balafilcon A, hilafilcon A, alphafilcon A, bilafilcon B and the like.

In one illustrative embodiment, a monomeric mixture will include a major amount of one or more non-silicone-containing hydrophilic monomers which are one or more cyclic lactams. In another illustrative embodiment, a monomeric mixture will include a major amount of one or more non-silicone-containing hydrophilic monomers which are N-vinyl caprolactam.

In an illustrative embodiment, the one or more hydrophilic monomers can be present in the monomeric mixture in an amount ranging from about 25 to about 90 wt. %, based on the total weight of the monomeric mixture. In another illustrative embodiment, the one or more hydrophilic monomers can be present in the monomeric mixture in an amount ranging from about 30 to about 75 wt. %, based on the total weight of the monomeric mixture.

In another embodiment, an ophthalmic device includes a device which is formed from materials which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed from a bulky silicone monomer (e.g., tris(trimethylsiloxy)silylpropyl methacrylate, commonly known as "TRIS" monomer), methacrylate end-capped poly (dimethylsiloxane)prepolymer, or silicones having fluoroalkyl side groups (polysiloxanes are also commonly known as silicone polymers).

Hydrogels in general are a well-known class of materials that comprise hydrated, crosslinked polymeric systems containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer can function as a crosslinking agent (a crosslinker being defined as a monomer having multiple polymerizable functionalities) or a separate crosslinker may be employed. Silicone hydrogels typically have a water content between about 10 to about 80 weight percent.

The monomer mixtures may also include a second device-forming monomer including a copolymerizable group and a reactive functional group. The copolymerizable group is preferably an ethylenically unsaturated group, such that this device-forming monomer copolymerizes with the hydrophilic device-forming monomer and any other device-forming monomers in the initial device-forming monomer mixture. Additionally, the second monomer can include a reactive functional group that reacts with a complementary reactive group of the resulting copolymer. In other words, after the device is formed by copolymerizing the device-forming monomer mixture, the reactive functional groups provided by the second device-forming monomers remain to react with a complementary reactive moiety of the copolymer.

In one embodiment, reactive groups of the second device-forming monomers include epoxide groups. Accordingly, second device-forming monomers are those that include both an ethylenically unsaturated group (that permits the monomer to copolymerize with the hydrophilic device-forming monomer) and the epoxide group (that does not react with the hydrophilic device-forming monomer but remains to react with a copolymer, e.g., the reaction product of one or more polymerizable polyhydric alcohols and one or more polymerizable fluorine-containing monomers). Suitable second device-forming monomers include, for example, glycidyl methacrylate, glycidyl acrylate, glycidyl vinylcarbonate, glycidyl vinylcarbamate, and 4-vinyl-1-cyclohexene-1,2-epoxide.

As mentioned, one class of ophthalmic device substrate materials are silicone hydrogels. In this case, the initial device-forming monomer mixture further comprises a silicone-containing monomer. Applicable silicone-containing monomeric materials for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of suitable materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

Representative examples of applicable silicone-containing monomers include are one or more non-bulky organosilicon-containing monomers. An "organosilicon-containing monomer" as used herein contains at least one [siloxanyl] or at least one [silyl-alkyl-siloxanyl] repeating unit, in a monomer, macromer or prepolymer. In one embodiment, an example of a non-bulky organosilicon-containing monomers is represented by a structure of Formula (Ia):

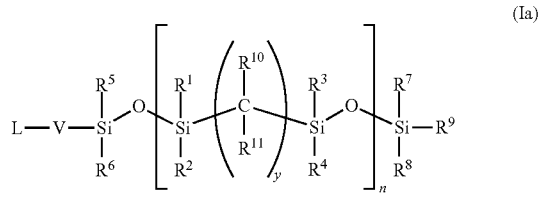

wherein L is ethylenically unsaturated polymerizable group, V is a linker group or a bond; $R^1$, $R^2$, $R^3$, $R^4$, $R^5$, $R^6$, $R^7$, $R^8$, and $R^9$ are independently hydrogen, an alkyl group, a haloalkyl group, a cycloalkyl group, a heterocycloalkyl group, an alkenyl group, a halo alkenyl group, or an aromatic group; $R^{10}$ and $R^{11}$ are independently hydrogen or alkyl wherein at least one of $R^{10}$ and $R^{11}$ is hydrogen; y is 2 to 7 and n is 1 to 100 or from 1 to 20.

Ethylenically unsaturated polymerizable groups are well known to those skilled in the art. Suitable ethylenically unsaturated polymerizable groups include, for example, (meth)acrylates, vinyl carbonates, O-vinyl carbamates, N-vinyl carbamates, and (meth)acrylamides.

Linker groups can be any divalent radical or moiety and include, for example, substituted or unsubstituted $C_1$ to $C_{12}$ alkyl, alkyl ether, alkenyls, alkenyl ethers, halo alkyls, substituted or unsubstituted siloxanes, and monomers capable of propagating ring opening.

In one embodiment, V is a (meth)acrylate, L is a $C_1$ to $C_{12}$ alkylene, $R^1$, $R^2$, $R^3$, $R^4$, $R^5$, $R^6$, $R^7$, $R^8$, and $R^9$ are independently a $C_1$ to $C_{12}$ alkyl, $R^{10}$ and $R^{11}$ are independently H, y is 2 to 7 and n is 3 to 8.

In one embodiment, V is a (meth)acrylate, L is a $C_1$ to $C_6$ alkyl, $R^1$, $R^2$, $R^3$, $R^4$, $R^5$, $R^6$, $R^7$, $R^8$, and $R^9$ are independently a $C_1$ to $C_6$ alkyl, $R^{10}$ and $R^{11}$ are independently H, y is 2 to 7 and n is 1 to 20.

Non-bulky organosilicon-containing monomers represented by a structure of Formula Ia are known in the art, see, e.g., U.S. Pat. Nos. 7,915,323, 7,994,356, 8,420,711, 8,827,447 and 9,039,174, the contents of which are incorporated by reference herein.

In an illustrative embodiment, one or more non-bulky organosilicon-containing monomers can comprise a compound represented by a structure of Formula (Ib):

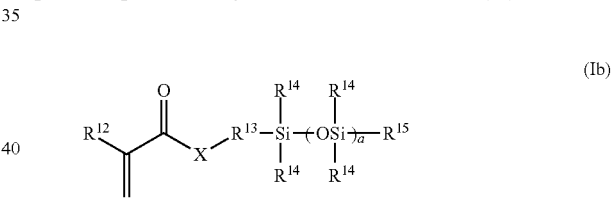

wherein $R^{12}$ is H or methyl; X is O or $NR^{16}$; wherein $R^{16}$ is selected from H, or $C_1$ to $C_4$ alkyl, which may be further substituted with one or more hydroxyl groups, and in some embodiments is H or methyl; $R^{13}$ is a divalent alkyl group, which may further be functionalized with a group selected from the group consisting of ether groups, hydroxyl groups, carbamate groups and combinations thereof, and in another embodiment $C_1$ to $C_6$ alkylene groups which may be substituted with ether, hydroxyl and combinations thereof, and in yet another embodiment $C_1$ or $C_3$ to $C_4$ alkylene groups which may be substituted with ether, hydroxyl and combinations thereof; each $R^{14}$ is independently a phenyl or $C_1$ to $C_4$ alkyl which may be substituted with fluorine, hydroxyl or ether, and in another embodiment each $R^{14}$ is independently selected from ethyl and methyl groups, and in yet another embodiment, each $R^{14}$ is methyl; $R^{15}$ is a $C_1$ to $C_4$ alkyl; a is 2 to 50, and in some embodiments 5 to 15.

Non-bulky organosilicon-containing monomers represented by a structure of Formula Ib are known in the art, see, e.g., U.S. Pat. Nos. 8,703,891, 8,937,110, 8,937,111, 9,156,934 and 9,244,197, the contents of which are incorporated by reference herein.

In one illustrative embodiment, the one or more non-bulky organosilicon-containing monomers can be present in the monomeric mixture in an amount ranging from about 5 wt. % to about 50 wt. %, based on the total weight of the monomeric mixture. In one embodiment, the one or more non-bulky organosilicon-containing monomers can be present in the monomeric mixture in an amount ranging from about 15 wt. % to about 45 wt. %, based on the total weight of the monomeric mixture.

Representative examples of applicable silicone-containing monomers also include bulky polysiloxanylalkyl(meth)acrylic monomers. An example of a bulky polysiloxanylalkyl(meth)acrylic monomer is represented by a structure of Formula (II):

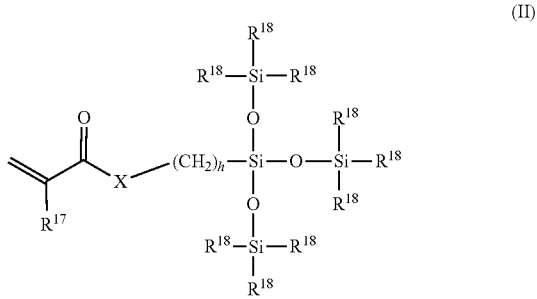

(II)

wherein X denotes —O— or —NR$^{19}$— where each R$^{19}$ is hydrogen or a C$_1$-C$_4$ alkyl; R$^{17}$ independently denotes hydrogen or methyl; each R$^{18}$ independently denotes a lower alkyl radical such as a C$_1$-C$_6$ group, a phenyl radical or a group represented by the following structure:

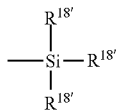

wherein each R$^{18'}$ independently denotes a lower alkyl radical or a phenyl radical; and h is 1 to 10; or the following structure of Formula (III):

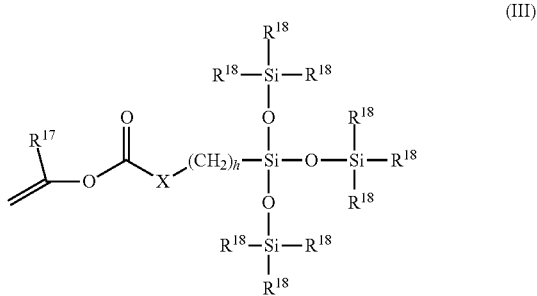

(III)

wherein X denotes —NR$^{19}$—; wherein R$^{19}$ denotes hydrogen or a C$_1$-C$_4$ alkyl; R$^{17}$ denotes hydrogen or methyl; each R$^{18}$ independently denotes a lower alkyl radical, a phenyl radical or a group represented by the following structure:

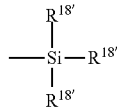

wherein each R$^{18'}$ independently denotes a lower alkyl radical or a phenyl radical; and his 1 to 10.

Examples of bulky monomers include methacryloxypropyl tris(trimethyl-siloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, for example, silicone-containing vinyl carbonate or vinyl carbamate monomers such as, for example, 1,3-bis[4-vinyloxycarbonyloxy)but-1-yl]tetramethyl-di siloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicone-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae (IV) and (V):

E(*D*A*D*G)$_a$*D*A*D*E'; or (IV)

E(*D*G*D*A)$_a$*D*A*D*E'; or (V)

wherein:
D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A independently denotes a divalent polymeric radical of Formula (VI):

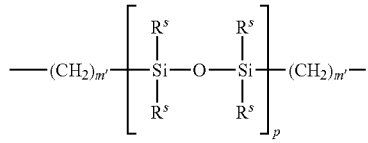
(VI)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula (VII):

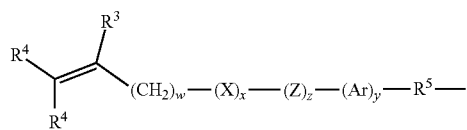
(VII)

wherein: $R^3$ is hydrogen or methyl;
$R^4$ is hydrogen, an alkyl radical having 1 to 6 carbon atoms, or a —CO—Y—$R^6$ radical wherein Y is —O—, —S— or —NH—;
$R^5$ is a divalent alkylene radical having 1 to about 10 carbon atoms;
$R^6$ is a alkyl radical having 1 to about 12 carbon atoms;
X denotes —CO— or —OCO—;
Z denotes —O— or —NH—;
Ar denotes an aromatic radical having about 6 to about 30 carbon atoms;
w is 0 to 6; x is 0 or 1; y is 0 or 1; and z is 0 or 1.

In one embodiment, a silicone-containing urethane monomer is represented by Formula (VIII):

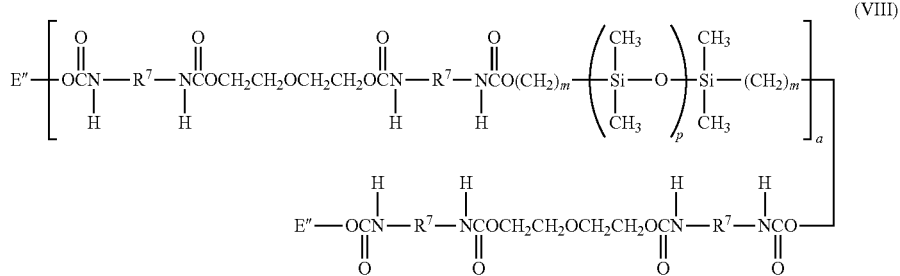
(VIII)

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

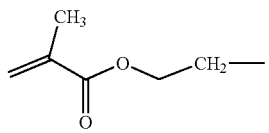

In another embodiment, a silicone hydrogel material comprises (in bulk, that is, in the monomer mixture that is copolymerized) about 5 to about 50 percent, or from about 10 to about 25, by weight of one or more silicone macromonomers, about 5 to about 75 percent, or about 30 to about 60 percent, by weight of one or more polysiloxanyl-alkyl (meth)acrylic monomers, and about 10 to about 50 percent, or about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the non-limiting embodiments described herein. The silane macromonomer may be a silicone-containing vinyl carbonate or vinyl carbamate or a polyurethane-polysiloxane having one or more hard-soft-hard blocks and end-capped with a hydrophilic monomer.

In another embodiment, another class of silicone-containing monomers includes monomers of Formula (IX):

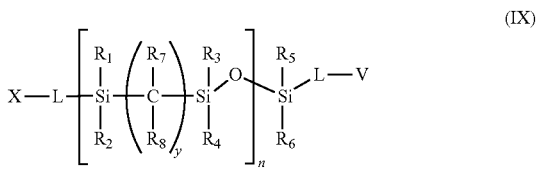
(IX)

wherein X is the residue of a ring opening agent; L is the same or different and is a linker group or a bond; V is an ethylenically unsaturated polymerizable group; $R_1$, $R_2$, $R_3$, $R_4$, $R_5$, $R_6$ are independently hydrogen, an alkyl group, a haloalkyl group, a cycloalkyl group, a heterocycloalkyl group, an alkenyl group, a halo alkenyl group, or an aromatic group; $R_7$ and $R_8$ are independently hydrogen or an alkyl group wherein at least one of $R_7$ or $R_8$ is hydrogen; y is 2-7 and n is 1-100.

Ring opening agents are well known in the literature. Non-limiting examples of anionic ring opening agents include alkyl lithium, an alkoxide, trialkylsiloxylithium wherein the alkyl group may or may not contain halo atoms.

Linker groups can be any divalent radical or moiety and include substituted or unsubstituted alkyl, alkyl ether, alkenyls, alkenyl ethers, halo alkyls, substituted or unsubstituted siloxanes, and monomers capable of propagating ring opening.

Ethylenically unsaturated polymerizable groups are well known to those skilled in the art. Non-limiting examples of ethylenically unsaturated polymerizable groups would include acrylates, methacrylates, vinyl carbonates, O-vinyl carbamates, N-vinyl carbamates, acrylamides and methacrylamides.

In another embodiment, a class of silicone-containing monomers includes monomers of Formula (X):

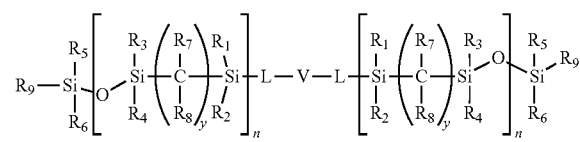

(X)

wherein L is the same or different and is a linker group or a bond; V is the same or different and is an ethylenically unsaturated polymerizable group; $R_1$, $R_2$, $R_3$, $R_4$, $R_5$, $R_6$ and $R_9$ are independently hydrogen, an alkyl group, a haloalkyl group, a cycloalkyl group, a heterocycloalkyl group, an alkenyl group, a halo alkenyl group, or an aromatic group; $R_7$ and $R_8$ are independently hydrogen or an alkyl group wherein at least one of $R_7$ or $R_8$ is hydrogen; y is 2-7 and n is 1-100.

In another embodiment, a class of silicone-containing monomers includes monomers of Formulas (XI) and (XII):

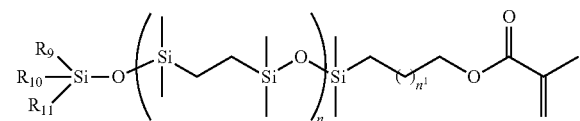

(XI)

wherein $R_9$, $R_{10}$ and $R_{11}$ are independently hydrogen, an alkyl group, a haloalkyl group or other substituted alkyl groups; n is as defined above and $n^1$ is 0-10; and,

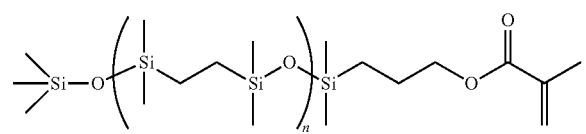

(XII)

wherein n is 1 to 100, or n is 2 to 80, or n is 3 to 20, or n is 5 to 15.

In another embodiment, a class of silicone-containing monomers includes monomers of Formulas (XIII)-(XVII):

(M1-EDS6-TMS)

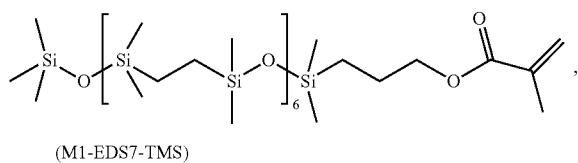

(XIII)

(M1-EDS7-TMS)

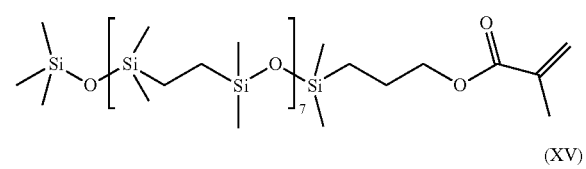

(XIV)

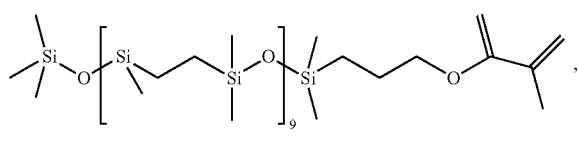

(XV)

(M1-EDS12-TMS)

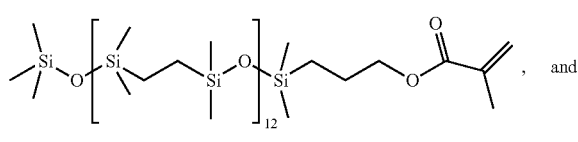

(XVI), and (M1-EDS15-TMS)

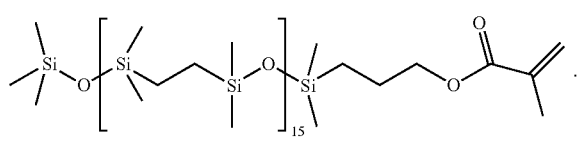

(XVII)

In another embodiment, a class of silicone-containing monomers includes monomers of Formulas (XVIII)-(XX):

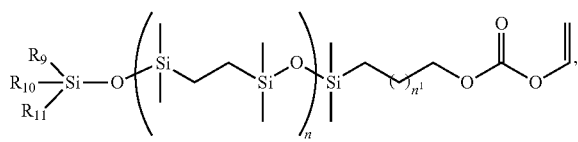

(XVIII)

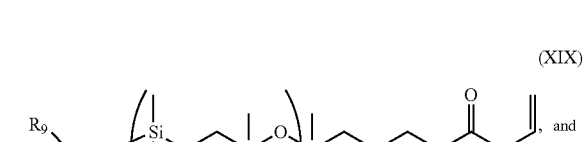

(XIX), and

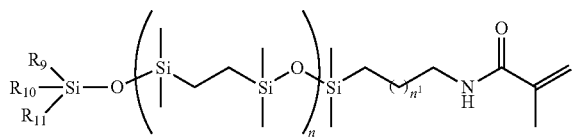

wherein $R_9$, $R_{10}$ and $R_{11}$ are independently hydrogen, an alkyl group, a haloalkyl group or other substituted alkyl groups and n and $n^1$ are as defined above.

In another embodiment, a class of silicons-containing monomers includes monomers of Formulas (XXI)-(XXIII):

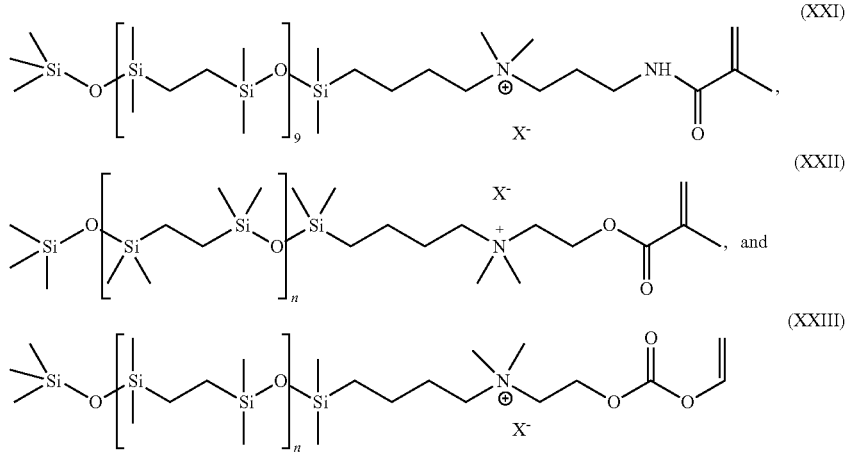

wherein n is as defined above and $X^-$ is a counterion to provide an overall neutral charge.

Counterions capable of providing an overall neutral charge are well known to those of ordinary skill in the art and would include, for example, halide ions.

In another embodiment, a class of silicone-containing monomers includes monomers of Formula (XXIV):

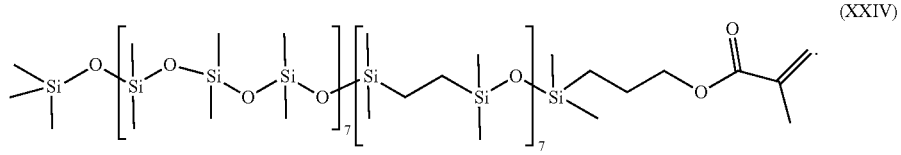

Representative examples of alkyl groups for use herein include, by way of example, a straight or branched alkyl chain radical containing carbon and hydrogen atoms of from 1 to about 30 carbon atoms or from 1 to about 12 carbon atoms or from 1 to about 6 carbon atoms with or without unsaturation, to the rest of the molecule, e.g., methyl, ethyl, n-propyl, 1-methylethyl (isopropyl), n-butyl, n-pentyl, methylene, ethylene, etc., and the like. The alkyl group can optionally contain one or more heteroatoms, e.g., 0 and N, and the like to form haloalkyl groups.

Representative examples of cycloalkyl groups for use herein include, by way of example, a substituted or unsubstituted non-aromatic mono or multicyclic ring system of about 3 to about 30 carbon atoms or from 3 to about 6 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4, 4)-non-2-yl and the like, optionally containing one or more heteroatoms, e.g., O and N, and the like to form halocycloalkyl groups.

Representative examples of aromatic groups for use herein include, by way of example, a substituted or unsubstituted monoaromatic or polyaromatic radical containing from about 6 to about 30 carbon atoms such as, for example, phenyl, naphthyl, tetrahydronapthyl, indenyl, biphenyl and the like, optionally containing one or more heteroatoms, e.g., O and N, and the like to form haloaromatic groups.

Representative examples of alkenyl groups for use herein include, by way of example, a substituted or unsubstituted alkyl group containing from about 2 to about 30 carbon atoms or from 3 to about 12 carbon atoms with at least one carbon-carbon double bond such as, for example, propenyl, butenyl, pentenyl and the like, wherein the alkenyl group can optionally contain one or more heteroatoms, e.g., O and N, and the like to form haloalkenyl groups.

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. Also, the use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates that have been disclosed in various publications and are being continuously developed for use in contact lenses and other ophthalmic devices can also be used. For example, an ophthalmic device can be formed from at least a cationic monomer such as cationic silicone-containing monomers or cationic fluorinated silicone-containing monomers.

Contact lenses for application of the illustrated embodiments described herein can be manufactured employing various conventional techniques, to yield a shaped article having the desired posterior and anterior lens surfaces. Spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

Once the ophthalmic devices such as contact lenses are dry released, they can then be subjected to optional machining operations. Other optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The resulting ophthalmic device thus formed is then subjected to the steps of the method according to illustrative non-limiting embodiments described herein to entrap the one or more red-light blocking compounds into the ophthalmic device. For example, in one step, the ophthalmic device is first soaked in one or more first solvent solutions for a time period sufficient to swell the ophthalmic device. In general, the one or more first solvent solutions include a solvent capable of swelling the ophthalmic device. In one embodiment, the one or more first solvent solutions include, for example, a low molecular weight alcohol solvent, an aliphatic hydrocarbon solvent, a cycloaliphatic hydrocarbon solvent, a ketone solvent, a nitrile solvent, an ether solvent, an amido group-containing solvent and mixtures thereof.

Suitable low molecular weight alcohols include, for example, low molecular weight alcohols having about 1 to about 13 carbon atoms and/or a molecular weight of no greater than about 200. A suitable low molecular alcohol can be selected from a variety of low-molecular-weight monohydric alcohols, each comprising about 1 to about 13 carbon atoms. Suitable monohydric alcohols include, for example, methanol, ethanol, propanol, isopropyl alcohol, butanol, isobutyl alcohol, tert-butyl alcohol, hexanol, 2-ethylhexanol, dodecanol, and the like. Suitable aliphatic or cycloaliphatic hydrocarbon solvents include, for example, pentane, hexane, heptane, cyclohexane and the like.

Suitable ketone solvents include, for example, acetone, methyl ethyl ketone, diethyl ketone, methyl propyl ketone, methyl isopropyl ketone, ethyl propyl ketone, ethyl isopropyl ketone, dipropyl ketone, diisopropyl ketone, methyl butyl ketone, methyl isobutyl ketone, methyl sec butyl ketone, methyl tert-butyl ketone, ethyl butyl ketone, ethyl isobutyl ketone, ethyl sec-butyl ketone, ethyl tert-butyl ketone, propyl butyl ketone, isopropyl butyl ketone, propyl isobutyl ketone, propyl sec-butyl ketone, propyl tert butyl ketone, isopropyl isobutyl ketone, isopropyl sec-butyl ketone, isopropyl tert-butyl ketone, dibutyl ketone, diisobutyl ketone, di-sec-butyl ketone, di-tert-butyl ketone, butyl isobutyl ketone, butyl sec-butyl ketone, butyl tert-butyl ketone, isobutyl sec-butyl ketone, isobutyl tert-butyl ketone, sec-butyl tert-butyl ketone, 5-heptanone, 5-methyl-2-hexanone (methyl isoamyl ketone), 4-methyl-2-hexanone, 3-methyl-2-hexanone, 3,4-dimethyl-2-pentanone, 3,3-dimethyl-2-pentanone, 4,4-dimethyl-2-pentanone, 3-octanone, 4-methyl-3-heptanone, 5-methyl-3-heptanone, 6-methyl-3-heptanone, 4,4-dimethyl-3-hexanone, 4,5-dimethyl-3-hexanone, 5,5-dimethyl-3-hexanone, 4-nonanone, 5-methyl-4-octanone, 6-methyl-4-octanone, 7-methyl-4-octanone, 5,5-dimethyl-4-neptanone, 5,6-dimethyl-4-heptanone, 6,6-dimethyl-4-heptanone, 2-undecanone, cyclopropanone, cyclobutanone, cyclopentanone, cyclohexanone, cycloheptanone, cyclooctanone, cyclononanone, cyclodecanone, cycloundecanone, cyclododecanone and the like and combinations thereof. In one embodiment, a ketone solvent is acetone.

Suitable nitrile solvents include, for example, saturated or unsaturated aliphatic, alicyclic, or aromatic compounds containing a nitrile group. Included within the nitriles are compounds containing heteroatom such as those selected from Groups 13, 14, 15, 16 and 17 of the Periodic Table of Elements. Representative examples of nitriles for use herein include acetonitrile; propionitrile; isopropionitrile; butyronitrile; isobutyronitrile; valeronitrile; isovaleronitrile; trimethylacetonitrile; hexanenitrile; heptanenitrile; heptyl cyanide; octyl cyanide; undecanenitrile; malononitrile; succinonitrile; glutaronitrile; adiponitrile; sebaconitrile; allyl cyanide; acrylonitrile; crotononitrile; methacrylonitrile; fumaronitrile; tetracyanoethylene; cyclopentanecarbonitrile; cyclohexanecarbonitrile; dichloroacetonitrile; fluoroacetonitrile; trichloroacetonitrile; benzonitrile; benzyl cyanide; 2-methylbenzylcyanide; 2-chlorobenzonitrile; 3-chlorobenzonitrile; 4-chlorobenzonitrile; o-tolunitrile; m-tolunitrile; p-tolunitrile and the like and mixtures thereof. In one embodiment, a a nitrile solvent is acetonitrile.

Suitable ether solvents include, for example, dialkyl ethers wherein the alkyl groups are the same or different and are from 1 to about 12 carbon atoms. Representative examples of an ether solvent include dimethylether, diethylether, di-i-propylether; dioxane, tetrahydrofuran, pyran and the like and mixtures thereof. In one embodiment, an ether solvent is tetrahydrofuran.

Suitable amido group-containing solvents include, for example, dimethyl formamide, N-methyl formanilide, N-formyl piperidine, N-formyl morpholine, dimethyl acetamide, N-methyl pyrrolidone, N,N-dimethyl benzamide and mixtures thereof. In one embodiment, an amido group-containing solvent is N-methyl pyrrolidone.

In one embodiment, the one or more first solvent solutions can further include water in combination with any of the foregoing first solvents. For example, the one or more first solvent solutions can be a blend containing from about 25 wt. % to about 75 wt. % of the one or more first solvent solutions and from about 75 wt. % to about 25 wt. % water. In another embodiment, a blend can contain from about 40 wt. % to about 60 wt. % of the one or more first solvent solutions and from about 60 wt. % to about 40 wt. % water.

The ophthalmic device is soaked in the one or more first solvent solutions for a time period sufficient to swell the ophthalmic device. In general, the ophthalmic device is soaked in the one or more first solvent solutions for a time period ranging from about 5 minutes to about 120 minutes. In one embodiment, the ophthalmic device is soaked in the one or more first solvent solutions for a time period ranging from about 5 minutes to about 60 minutes. In one embodiment, the ophthalmic device is soaked in the one or more first solvent solutions for a time period ranging from about 10 minutes to about 35 minutes.

In illustrative embodiments, the ophthalmic device is soaked in a series of the one or more first solvent solutions. For example, the ophthalmic device is first soaked in the one or more first solvent solutions or a blend of the one or more first solvents and water as discussed hereinabove for a time period ranging from about 5 minutes to about 30 minutes, or from about 5 minutes to about 20 minutes. Next, the ophthalmic device is removed from the solution or blend and soaked in another solvent solution of any of the foregoing one or more first solvents or blend of the one or more first solvents and water as discussed hereinabove for a time period ranging from about 5 minutes to about 120 minutes. In an embodiment, the ophthalmic device is soaked in another solvent solution of any of the foregoing one or more first solvents or blend of the one or more first solvents and water as discussed hereinabove for a time period ranging from about 5 minutes to about 60 minutes. In another embodiment, the ophthalmic device is soaked in yet another solvent solution of any of the foregoing one or more first solvents or blend of the one or more first solvents and water as discussed hereinabove for a time period ranging from about 10 minutes to about 35 minutes.

In another step, the swelled ophthalmic device is soaked in one or more second solvent solutions comprising the one or more red-light blocking compounds to de-swell the ophthalmic device and entrap the one or more red-light blocking compounds in the ophthalmic device. In illustrative embodiments, the one or more second solvent solutions include any solvent capable of dissolving the one or more red-light blocking compounds. Suitable second solvent solutions include, for example, water alone or with any of the foregoing low molecular weight alcohol solvent, aliphatic hydrocarbon solvent, cycloaliphatic hydrocarbon solvent, ketone solvent, nitrile solvent, ether solvent, and amido group-containing solvents discussed hereinabove. In an illustrative embodiment, the second solvent solution is water alone.

In an embodiment, the one or more second solvent solutions include a blend of water together with any of the low molecular weight alcohol solvents, aliphatic hydrocarbon solvents, cycloaliphatic hydrocarbon solvents, ketone solvents, nitrile solvents, ether solvents, and amido group-containing solvent. For example, the one or more second solvent solutions can be a blend containing from about 25 wt. % to about 75 wt. % of the one or more second solvent solutions such as a low molecular weight alcohol and from about 75 wt. % to about 25 wt. % water. In another embodiment, a blend can contain from about 40 wt. % to about 60 wt. % of the one or more second solvent solutions such as a low molecular weight alcohol and from about 60 wt. % to about 40 wt. % water. When using a blend, the one or more red-light blocking compounds are first added to the one or more second solvent solutions to form a solution. Next, water is added to the solution in an amount such that the one or more red-light blocking compounds do not precipitate out of the solution.

In non-limiting illustrative embodiments, when soaking the swelled ophthalmic device in the one or more second solvent solutions comprising the one or more red-light blocking compounds to de-swell the ophthalmic device, at least a portion of the one or more red-light blocking compounds may covalently bond with a reactive functionality on the lens via hydrogen bonding. For example, when the ophthalmic device is derived from a polymerization product of a monomeric mixture comprising one or more non-silicone hydrophilic monomers having OH reactive groups present on the surface of the lens or in the lens such as 2-hydroxyethylmethacrylate and glycidyl methacrylate, the OH groups of the one or more non-silicone hydrophilic monomers can react with a reactive functionality complementary to the OH groups via hydrogen bonding. This is illustrated below in the non-limiting embodiment of Scheme I.

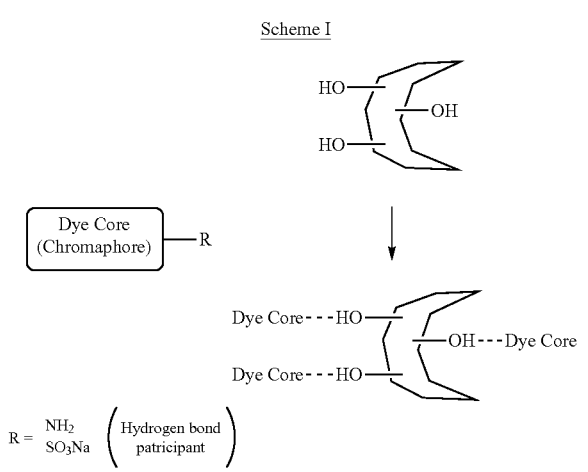

In illustrative embodiments, the one or more red-light blocking compounds are present in the one or more second solvent solutions in an amount ranging from about 0.05 to about 5 wt. %, based on the total weight of the solution. In an illustrative embodiment, the one or more red-light blocking compounds are present in the one or more second solvent solutions in an amount ranging from about 0.50 to about 1.5 wt. %, based on the total weight of the solution.

The ophthalmic device is soaked in the one or more second solvent solutions for a time period sufficient to de-swell the ophthalmic device and entrap the one or more red-light blocking compounds. In an illustrative embodiment, the ophthalmic device is soaked in the one or more second solvent solutions for a time period ranging from about 5 minutes to about 120 minutes. In another illustrative embodiment, the ophthalmic device is soaked in the one or more second solvent solutions for a time period ranging from about 10 minutes to about 18 hours.

In illustrative embodiments, the ophthalmic device can be soaked in a series of the one or more second solvent solutions. For example, the ophthalmic device is first soaked in one or more second solvent solutions comprising water alone or a low molecular weight alcohol solvent together with the one or more of the red-light blocking compounds for a time period ranging from about 5 minutes to about 30 minutes or from about 10 minutes to about 18 hours. Next, the ophthalmic device is removed from the solvent solution and further soaked in one or more additional solvent solutions containing one or more of the red-light blocking compounds for a time period ranging from about 5 minutes to about 30 minutes. In one embodiment, the one or more additional solvent solutions can comprise a blend of the same or different low molecular weight alcohol solvents and water and one or more of the red-light blocking compounds followed by another solvent solution of water and one or more of the red-light blocking compounds.

In illustrative embodiments, the one or more red-light blocking compounds comprise one or more red-light blocking compounds blocking from greater than about 5% to about 25% of red-light transmission through the ophthalmic device at a wavelength of from about 550 nm to about 800 nm. In an illustrative embodiment, the one or more red-light blocking compounds comprise one or more red-light blocking compounds blocking greater than about 5% to about 25% of red-light transmission through the ophthalmic device at a wavelength of from about 550 nm to about 700 nm. In an illustrative embodiment, the one or more red-light blocking compounds comprise one or more red-light blocking compounds blocking greater than about 5% to about 25% of red-light transmission through the ophthalmic device at a wavelength of from about 650 nm to about 680 nm.

In illustrative embodiments, the one or more red-light blocking compounds comprise one or more red-light blocking compounds blocking from about 10% to about 15% of red-light transmission through the ophthalmic device at a wavelength of from about 550 nm to about 800 nm. In an illustrative embodiment, the one or more red-light blocking compounds comprise one or more red-light blocking compounds blocking from about 10% to about 15% of red-light transmission through the ophthalmic device at a wavelength of from about 550 nm to about 700 nm. In an illustrative embodiment, the one or more red-light blocking compounds comprise one or more red-light blocking compounds blocking greater from about 10% to about 15% of red-light transmission through the ophthalmic device at a wavelength of from about 650 nm to about 680 nm.

In illustrative embodiments, representative examples of suitable red-light blocking compounds for use herein are represented by the following compounds I-IX.

Compound I

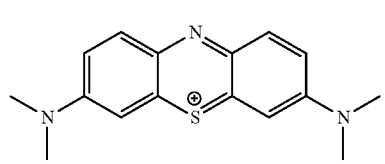

Compound II

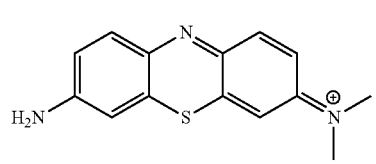

Compound III

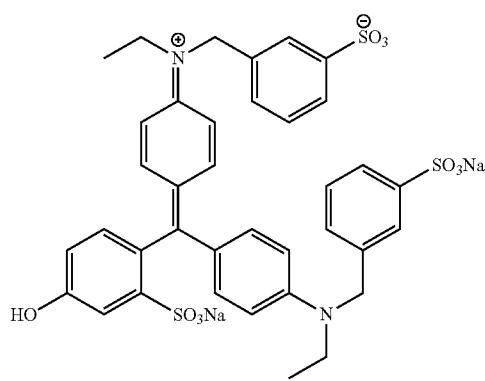

Compound IV

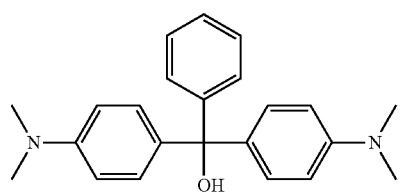

Compound V

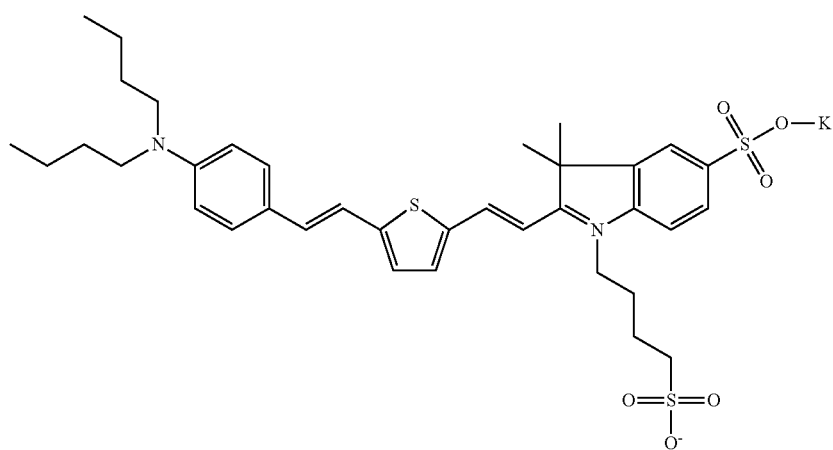

-continued

Compound VI

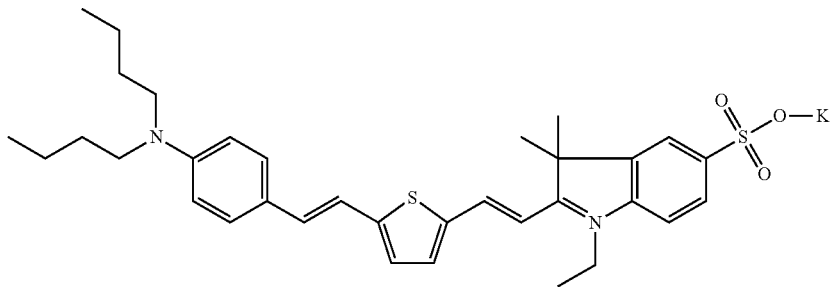

Compound VII

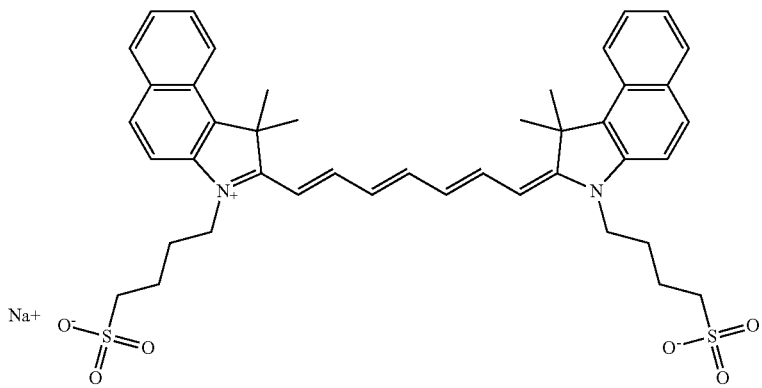

Compound VIII

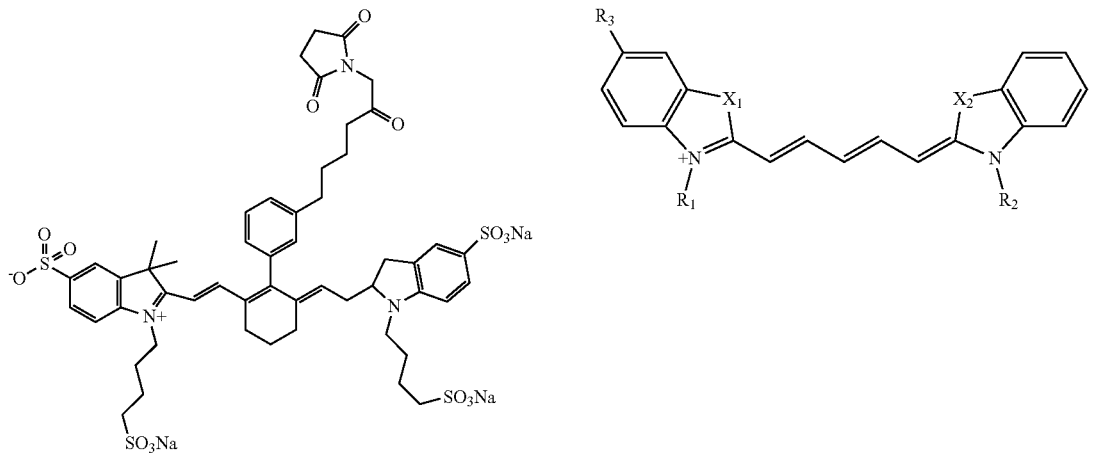

Compound IX wherein $X_1$ and $X_2$ are independently $CH_2$ or $C(CH_3)_2$; $R_1$ and $R_2$ are independently H or $(CH_2)_4SO_3Na$, and $R_3$ is H or $SO_3Na$.

The one or more red-light blocking compounds can be obtained by methods known in the art or are commercially available from such sources as LI-COR Biosciences, Inc.

After the ophthalmic device has been de-swelled, the ophthalmic device is removed and optionally soaked in one more series of water solutions to further de-swell the device. In an illustrative embodiment, the ophthalmic device is soaked in one or more of the water solutions for a time period each ranging from about 5 minutes to about 20 minutes.

In another step, the de-swelled ophthalmic device is sterilized. In an illustrative embodiment, the de-swelled ophthalmic device is sterilized by submerging the de-swelled ophthalmic device in a suitable buffered saline such as a borate buffered saline and then subjecting it to autoclave conditions for at least about 5 minutes. In an illustrative embodiment, the de-swelled ophthalmic device is subjected to autoclave conditions for at least about 20 minutes. In another illustrative embodiment, the de-swelled ophthalmic device is subjected to autoclave conditions for at least 1 hour. The sterilized ophthalmic device is then rinsed with water and positioned in their packaging with borate buffered saline. The package is sealed and again the ophthalmic device is subjected to autoclave conditions.

Alternatively, the de-swelled ophthalmic device can be placed in a container that includes a receptacle portion to hold the de-swelled ophthalmic device and a sterile packaging solution. Examples of the container are conventional ophthalmic device blister packages. This receptacle, containing the de-swelled ophthalmic device immersed in the solution, is hermetically sealed, for example, by sealing lidstock on the package over the receptacle. For example, the lidstock is sealed around a perimeter of the receptacle.

The solution and the de-swelled ophthalmic device are sterilized while sealed in the package receptacle. Examples of sterilization techniques include subjecting the solution and the de-swelled ophthalmic device to thermal energy, microwave radiation, gamma radiation or ultraviolet radiation. A specific example involves heating the solution and the de-swelled ophthalmic device, while sealed in the package container, to a temperature of at least about 100° C., or at about least about 121° C., such as by autoclaving.

The following examples are provided to enable one skilled in the art to practice the invention and are merely illustrative. The examples should not be read as limiting the scope of the invention as defined in the claims.

In the examples, the following abbreviations are used.
DMA: N,N-dimethylacrylamide.
HEMA: 2-hydroxyethyl methacrylate.
NVP: N-vinyl-2-pyrrolidone.
EGDMA: Ethylene glycol dimethacrylate.
SIGMA: (3-methacryloxy-2-hydroxypropoxy)propyl bis(trimethylsiloxy)methylsilane
TRIS: 3-[Tris(trimethylsiloxy)silyl]propyl methacrylate.
Irgacure 819: a photoinitiator for free radical polymerization available from Sigma Aldrich.
CIX-4: a compound having the structure:

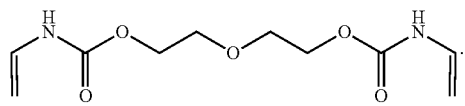 [SMILES: C=CNC(=O)OCCOCCOC(=O)NC=C]

Ma2D37: a compound having the following structure and available from Shin-Etsu or Gelest:

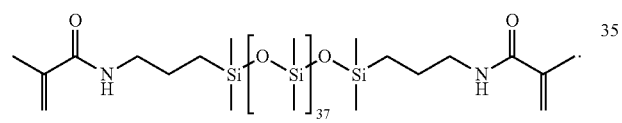

M1EDS6: a compound having the following structure and available from Gelest:

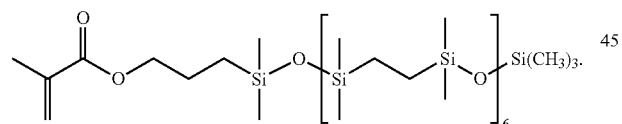

EXAMPLE 1

A red-light blocker having the following structure was used in this example.

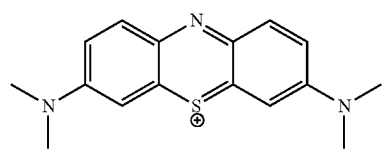

The ophthalmic lens used in this example was prepared per methods known in the art from the formulation set forth below in Table 1, where the components are listed in amounts per weight.

TABLE 1

| Formulation | |
|---|---|
| Tris | 31.30 |
| Ma2D37 | 5.40 |
| M1EDS6 | 14.10 |
| NVP | 32.40 |
| EGDMA | 0.14 |
| HEMA | 1.90 |
| DMA | 7.10 |
| Hexanol | 7.30 |
| Irgacure 819 | 0.30 |
| CIX-4 | 0.06 |

The ophthalmic lens was soaked in a series of solutions beginning with a 50:50 isopropyl alcohol (IPA):H$_2$O solution for 10 minutes, followed by 100% IPA for 30 minutes, followed by 50:50 IPA:H$_2$O solution for 10 minutes followed by 2×100% water for 10 minutes each. Next, the lens was soaked in a 0.5 wt. % solution of the red-light blocker in water with agitation for 18 hours. The lens was then extracted with in water 3 times for 20 minutes each. The lens was then placed in a vial containing a borate buffer solution and autoclaved. The lens was then individually placed onto a horizontal integrating sphere for contact lens measurement. The transmittance spectrum was obtained from 200 nm to 800 nm. FIG. 1 is a graph illustrating the percent transmission of red-light through the lens subjected to the steps of Example 1.

EXAMPLE 2

A red-light blocker having the following structure was used in this example.

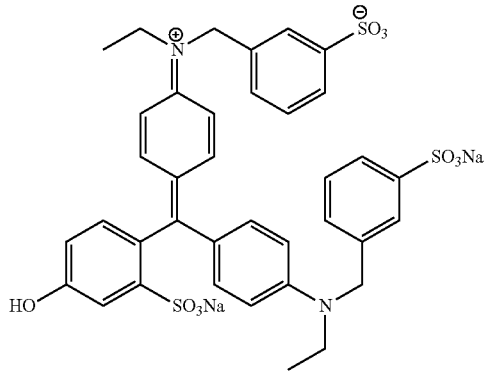

The ophthalmic lens used in this example was prepared per methods known in the art from the formulation set forth below in Table 2, where the components are listed in amounts per weight.

TABLE 2

| Formulation | |
|---|---|
| Tris | 31.30 |
| Ma2D37 | 5.40 |
| M1EDS6 | 14.10 |
| NVP | 32.40 |
| EGDMA | 0.14 |
| HEMA | 1.90 |
| DMA | 7.10 |

TABLE 2-continued

| Formulation | |
|---|---|
| Hexanol | 7.30 |
| Irgacure 819 | 0.30 |
| CIX-4 | 0.06 |

The ophthalmic lens is soaked in a series of solutions beginning with a 50:50 IPA:H₂O solution for 10 minutes, followed by 100% IPA for 30 minutes, followed by 50:50 IPA:H₂O solution for 10 minutes followed by 3×100% water for 20 minutes each. Next, the lens is soaked in a 0.2 wt. % solution of the red-light blocker in water at room temperature for 18 hours, followed by 50:50 IPA:H₂O solution for 10 minutes followed by 3×100% water for 20 minutes each. The lens is then placed in a vial containing a borate buffer solution and autoclaved.

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present compositions and are disclosed herein just as if each and every such sub-combination was individually and explicitly disclosed herein.

It will be understood that various modifications may be made to the illustrative non-limiting embodiments disclosed herein. Therefore, the above description should not be construed as limiting, but merely as exemplifications of preferred embodiments. For example, the functions described above and implemented as the best mode for operating the illustrative non-limiting embodiments are for illustration purposes only. Other arrangements and methods may be implemented by those skilled in the art without departing from the scope and spirit herein. Moreover, those skilled in the art will envision other modifications within the scope and spirit of the features and advantages appended hereto.

What is claimed is:

1. A method for preparing an ophthalmic device containing one or more red-light blocking compounds, the method comprising:
   (a) soaking an ophthalmic device in one or more first solvent solutions to swell the ophthalmic device;
   (b) soaking the swelled ophthalmic device in one or more second solvent solutions comprising one or more red-light blocking compounds blocking greater than about 5% to about 25% of red-light transmission through the ophthalmic device at a wavelength of from about 550 nanometers (nm) to about 800 nm to de-swell the swelled ophthalmic device and entrap the one or more red-light blocking compounds in the de-swelled ophthalmic device; and
   (c) sterilizing the de-swelled ophthalmic device;
   wherein the one or more first solvent solutions comprise a blend of a low molecular weight alcohol solvent and water, and the ophthalmic device is soaked in the one or more first solvent solutions for a time period ranging from about 5 minutes to about 120 minutes.

2. The method according to claim 1, wherein the one or more red-light blocking compounds comprise one or more red-light blocking compounds blocking greater than about 5% to about 25% of red-light transmission through the ophthalmic device at a wavelength of from about 550 nm to about 700 nm.

3. The method according to claim 1, wherein the one or more red-light blocking compounds comprise one or more red-light blocking compounds blocking greater than about 5% to about 25% of red-light transmission through the ophthalmic device at a wavelength of from about 650 nm to about 680 nm.

4. The method according to claim 1, wherein the one or more second solvent solutions comprise water or a blend of a low molecular weight alcohol solvent and water, and the ophthalmic device is soaked in the one or more second solvent solutions for a time period ranging from about 10 minutes to about 18 hours.

5. The method according to claim 1, wherein the one or more red-light blocking compounds are present in the one or more second solvent solutions in an amount ranging from about 0.05 to about 5 wt. %, based on the total weight of the one or more second solvent solutions.

6. The method according to claim 1, further comprising soaking the de-swelled ophthalmic device in water to further de-swell the de-swelled ophthalmic device prior to step (c).

7. The method according to claim 1, wherein step (c) comprises autoclaving the de-swelled ophthalmic device.

8. The method according to claim 1, wherein the ophthalmic device is one or more of a contact lens, an intraocular lens and a corneal implant.

9. The method according to claim 1, wherein the one or more red-light blocking compounds are represented by one or more of the following compounds:

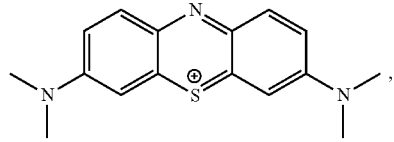

Compound I

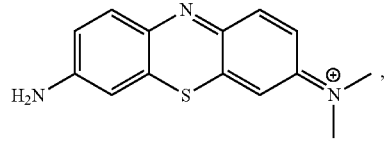

Compound II

-continued
Compound III
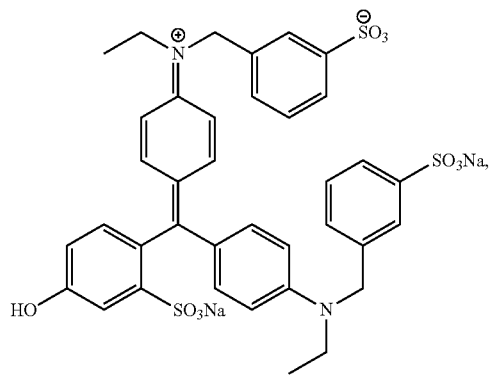
Compound IV
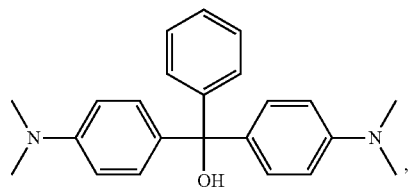
Compound V
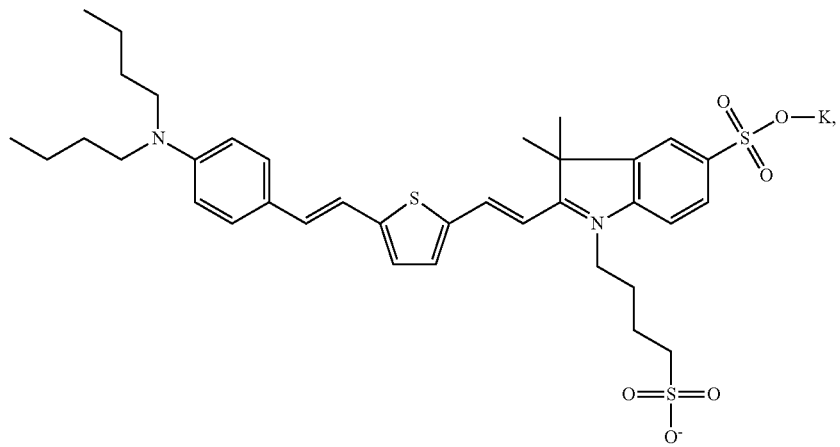
Compound VI
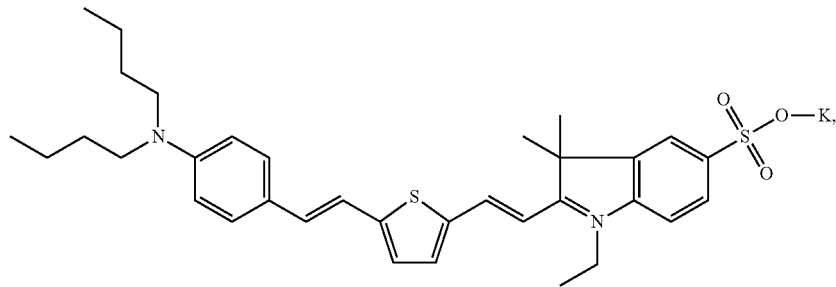
Compound VII
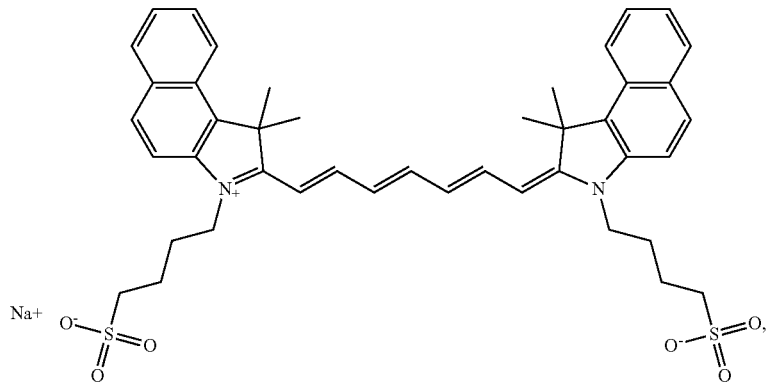

Compound VIII

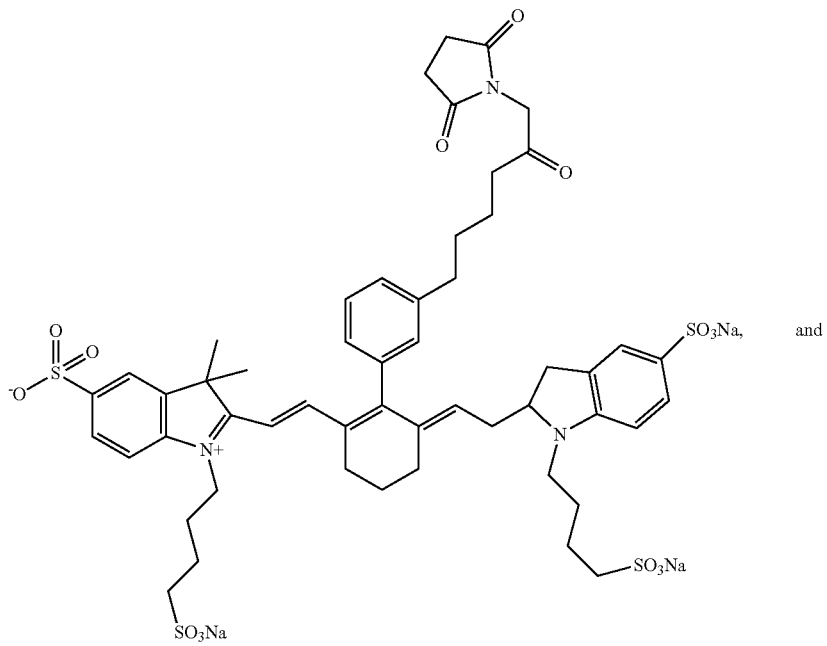

and

Compound IX

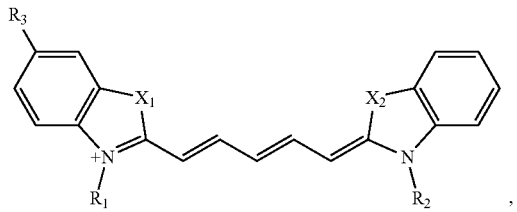

wherein $X_1$ and $X_2$ are independently $CH_2$ or $C(CH_3)_2$; $R_1$ and $R_2$ are independently H or $(CH_2)_4SO_3Na$, and $R_3$ is H or $SO_3Na$.

10. A method for preparing an ophthalmic device containing one or more red-light blocking compounds, the method comprising:
(a) soaking an ophthalmic device in one or more first solvent solutions to swell the ophthalmic device;
(b) soaking the swelled ophthalmic device in one or more second solvent solutions comprising one or more red-light blocking compounds blocking greater than about 5% to about 25% of red-light transmission through the ophthalmic device at a wavelength of from about 550 nanometers (nm) to about 800 nm to de-swell the swelled ophthalmic device and entrap the one or more red-light blocking compounds in the de-swelled ophthalmic device; and
(c) sterilizing the de-swelled ophthalmic device;
wherein step (a) comprises:
(i) soaking the ophthalmic device in the one or more first solvent solutions comprising a blend of a low molecular weight alcohol solvent and water for a time period ranging from about 5 minutes to about 120 minutes; and (ii) soaking the ophthalmic device of step (i) in one or more additional solvent solutions each comprising one or more of the same or different low molecular weight alcohol solvent, an aliphatic hydrocarbon solvent, a cycloaliphatic hydrocarbon solvent, a ketone solvent, a nitrile solvent, an ether solvent, an amido group-containing solvent and water for a time period ranging from about 5 minutes to about 60 minutes.

11. The method according to claim 10, wherein the one or more red-light blocking compounds comprise one or more red-light blocking compounds blocking greater than about 5% to about 25% of red-light transmission through the ophthalmic device at a wavelength of from about 550 nm to about 700 nm.

12. The method according to claim 10, wherein the one or more red-light blocking compounds comprise one or more red-light blocking compounds blocking greater than about 5% to about 25% of red-light transmission through the ophthalmic device at a wavelength of from about 650 nm to about 680 nm.

13. The method according to claim 10, wherein the one or more red-light blocking compounds are represented by one or more of the following compounds:

Compound I
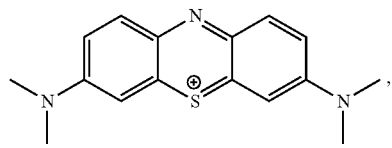
Compound II
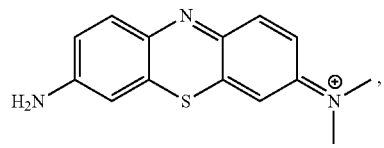
Compound III
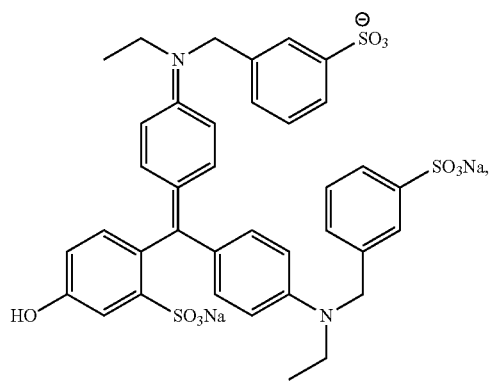
Compound IV
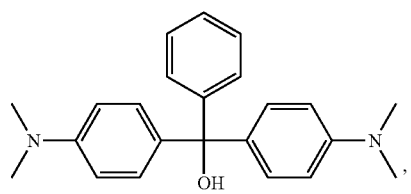
Compound V
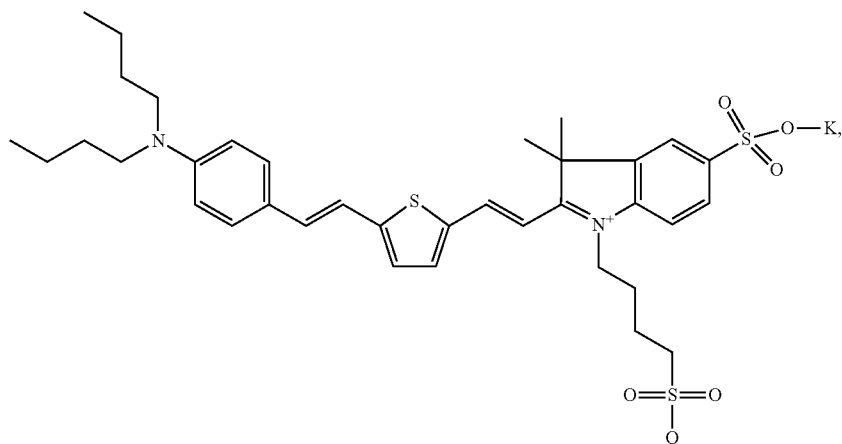
Compound VI
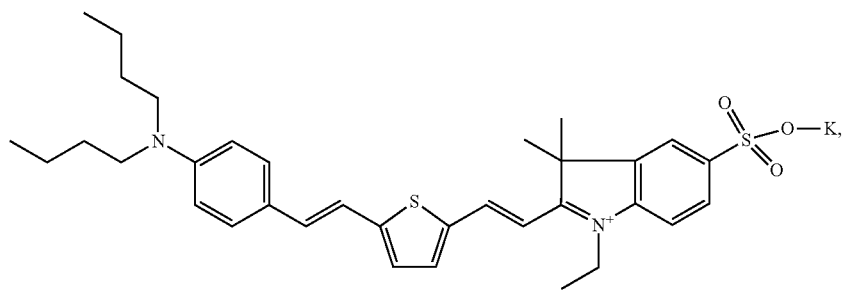

Compound VII

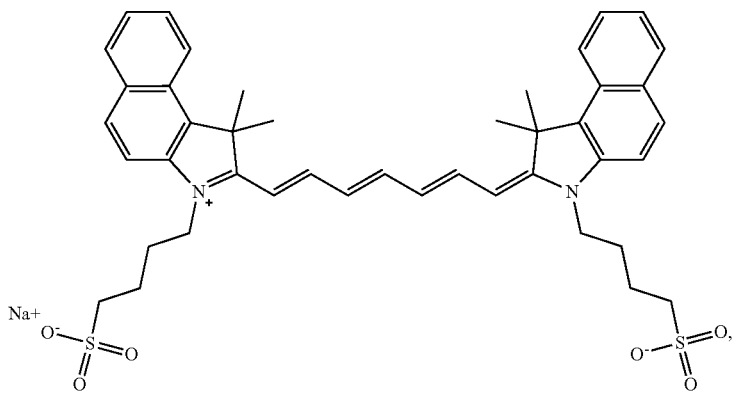

Compound VIII

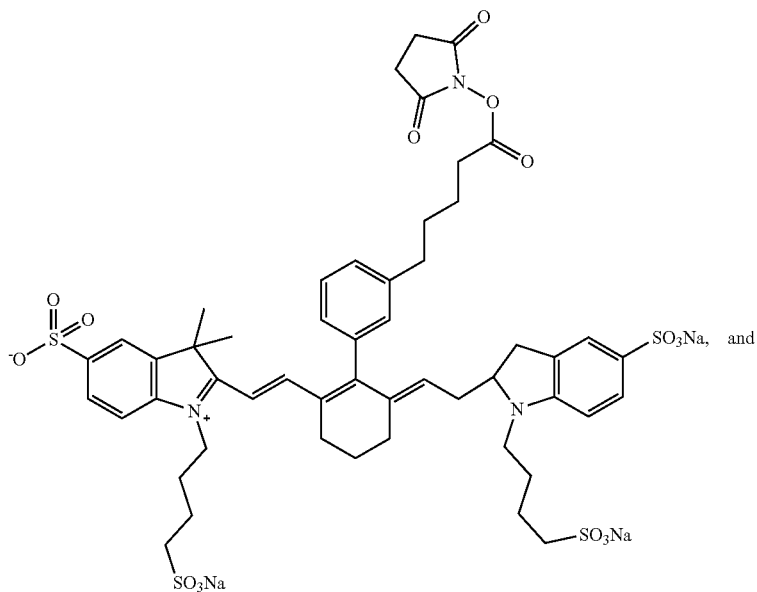

and

Compound IX

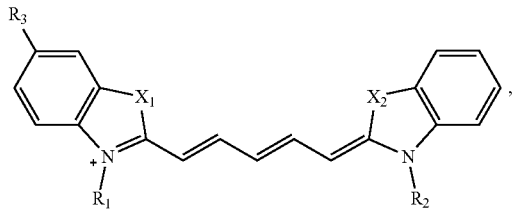

wherein $X_1$ and $X_2$ are independently $CH_2$ or $C(CH_3)_2$; $R_1$ and $R_2$ are independently H or $(CH_2)_4SO_3Na$, and $R_3$ is H or $SO_3Na$.

14. The method according to claim 10, wherein the one or more second solvent solutions comprise water or a blend of a low molecular weight alcohol solvent and water, and the ophthalmic device is soaked in the one or more second solvent solutions for a time period ranging from about 10 minutes to about 18 hours.

15. The method according to claim 10, wherein the one or more red-light blocking compounds are present in the one or more second solvent solutions in an amount ranging from about 0.05 to about 5 wt. %, based on the total weight of the one or more second solvent solutions.

16. The method according to claim 10, further comprising soaking the de-swelled ophthalmic device in water to further de-swell the de-swelled ophthalmic device prior to step (c).

17. The method according to claim 10, wherein step (c) comprises autoclaving the de-swelled ophthalmic device.

18. The method according to claim 10, wherein the ophthalmic device is one or more of a contact lens, an intraocular lens and a corneal implant.

19. A method for preparing an ophthalmic device containing one or more red-light blocking compounds, the method comprising:
(a) soaking an ophthalmic device in one or more first solvent solutions to swell the ophthalmic device;
(b) soaking the swelled ophthalmic device in one or more second solvent solutions comprising one or more red-light blocking compounds blocking greater than about 5% to about 25% of red-light transmission through the ophthalmic device at a wavelength of from about 550 nanometers (nm) to about 800 nm to de-swell the swelled ophthalmic device and entrap the one or more red-light blocking compounds in the de-swelled ophthalmic device; and
(c) sterilizing the de-swelled ophthalmic device;
wherein the one or more red-light blocking compounds are represented by one or more of the following compounds:

Compound I
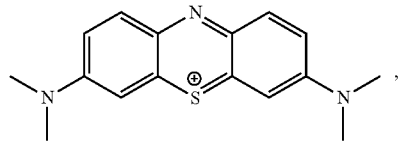

Compound II
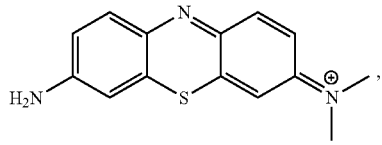

Compound III
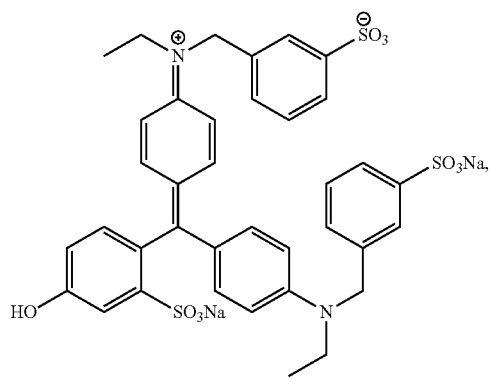

Compound IV
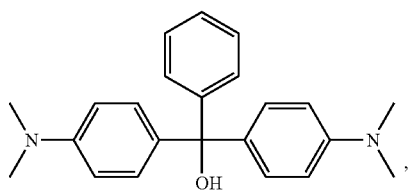

Compound V
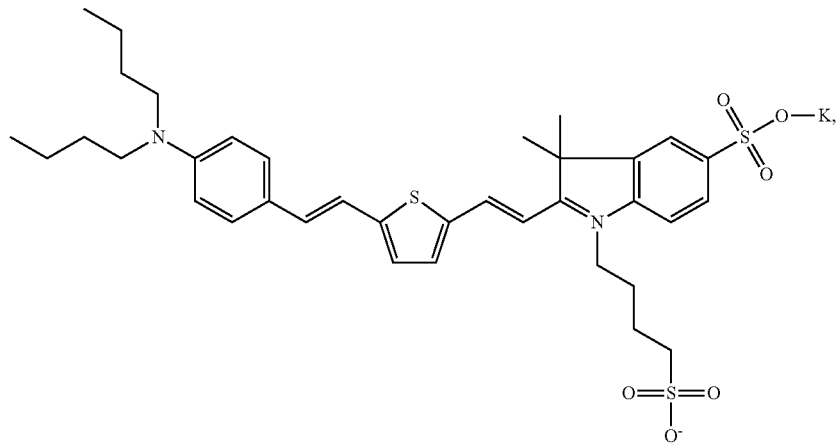

Compound VI
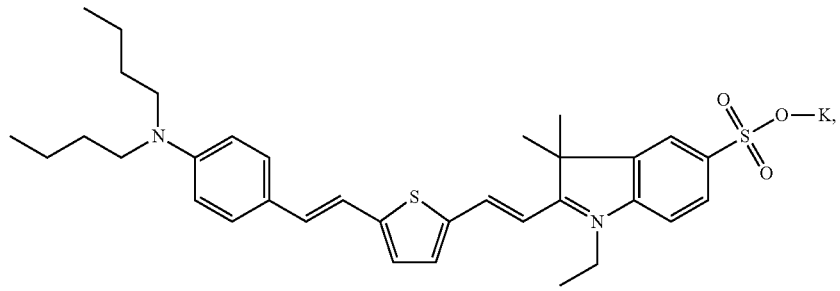

-continued

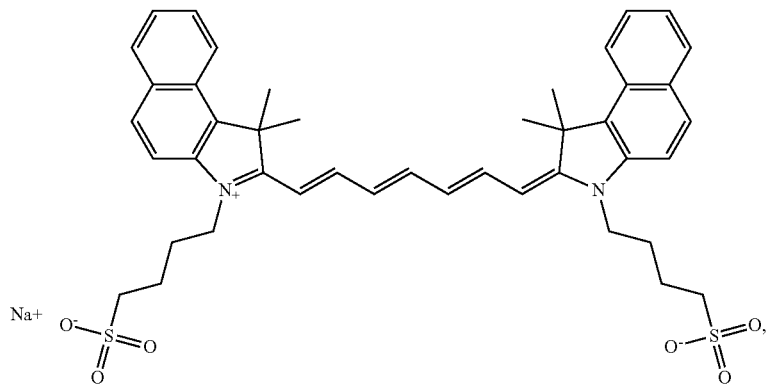

Compound VII

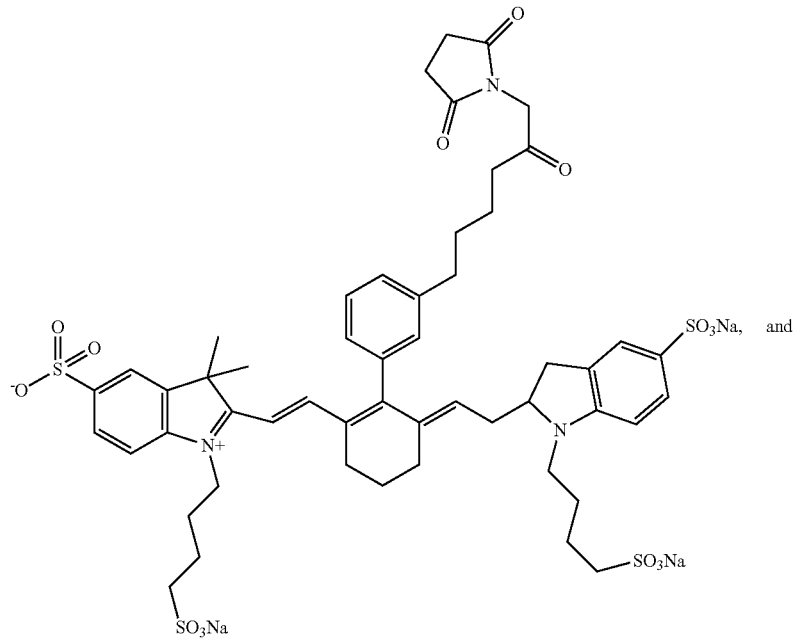

Compound VIII

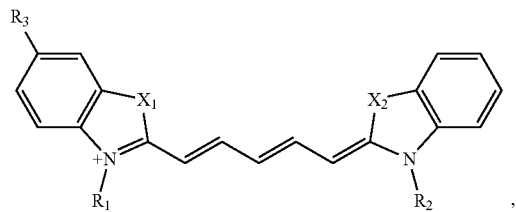

Compound IX wherein $X_1$ and $X_2$ are independently $CH_2$ or $C(CH_3)_2$; $R_1$ and $R_2$ are independently H or $(CH_2)_4SO_3Na$, and $R_3$ is H or $SO_3Na$.

20. The method according to claim 19, wherein the one or more red-light blocking compounds are present in the one or more second solvent solutions in an amount ranging from about 0.05 to about 5 wt. %, based on the total weight of the one or more second solvent solutions, and the ophthalmic device is one or more of a contact lens, an intraocular lens and a corneal implant.

* * * * *